United States Patent [19]

Skaar et al.

[11] 4,003,878

[45] Jan. 18, 1977

[54] METHOD OF PREPARING AN ALKALI-METAL SALT OF AN ALKOXYSULFONATED BENZOIC ACID GLYCOL ESTER

[75] Inventors: Thomas F. Skaar, Wilmington, Del.; John A. Price, Swarthmore, Pa.

[73] Assignee: Avtex Fibers Inc., Valley Forge, Pa.

[22] Filed: Mar. 26, 1973

[21] Appl. No.: 345,230

Related U.S. Application Data

[63] Continuation of Ser. No. 313,140, Dec. 7, 1972, abandoned.

[52] U.S. Cl. ............................ 260/49; 260/75 S; 260/470
[51] Int. Cl.² ........................................ C08G 63/68
[58] Field of Search .................. 260/49, 470, 75 S

[56] References Cited

UNITED STATES PATENTS 3,663,508   5/1972   Mobius et al. .................. 260/49

*Primary Examiner*—Lester L. Lee
*Attorney, Agent, or Firm*—Arthur R. Eglington

[57] ABSTRACT

An alkali-metal salt of an alkoxysulfonated benzoic acid glycol ester is prepared by reacting a meta- or para-hydroxy substituted benzoic acid with an alkali-metal alkoxide and a solvent reactant consisting essentially of an alkylene glycol, and then reacting the formed glycol ester with an alkane sultone.

8 Claims, No Drawings

METHOD OF PREPARING AN ALKALI-METAL SALT OF AN ALKOXYSULFONATED BENZOIC ACID GLYCOL ESTER

This application is a continuation of copendng application Ser. No. 313,140, filed Dec. 7, 1972 and now abandoned.

Alkali-metal salts of alkoxysulfonated aromatic carboxylic acids have been found useful as comonomers in the preparation of cationic dyeable, filament-forming copolyester resins. In the past, these comonomers have been prepared by reacting a hydroxy substituted aromatic acid ester with an alkane sultone in an alkanolic solution. For example, see U.S. Pat. No. 3,663,508 and West German Pat. No. 743,570. It has now been found that several advantages result by forming the salt in a modified process.

It is a principal object of this invention to provide a method for the formation of an alkali-metal salt of an alkoxysulfonated aromatic carboxylic acid wherein the product need not be isolated from the solvent used for its preparation.

This and other objects are accomplished in accordance with this invention by reacting a monoalkyl ester of a meta- or para-hydroxy substituted benzoic acid wherein the alkyl group has from 1 to 6 carbon atoms with an alkali-metal alkoxide having from 1 to 4 carbon atoms and a solvent-reactant consisting essentially of an alkylene glycol having from 2 to 10 carbon atoms or diethylene glycol whereby a glycol ester of an alkali-metal oxy substituted aromatic carboxylic acid is formed, and reacting said glycol ester with an alkane sultone having from 3 to 4 carbon atoms to form an alkali-metal salt of an alkoxysulfonated carboxylic acid ester of an alkylene glycol dissolved in said solvent-reactant. This resulting solution is then used in a transesterification-polycondensation procedure with the addition of dialkyl terephthalate or the like and more glycol. Alternatively, the resulting solution is combined with the prepolymer or low molecular weight product of the direct esterification of terephthalic acid and alkylene glycol along with additional glycol and the combination polycondensed. If desired, such as when the solution is to be added directly to a direct esterification reaction, the alkanol formed or present during the initial reaction can be distilled off.

Alkyl esters of the benzoic acids include methyl esters, ethyl esters, propyl esters, butyl esters, pentyl esters and hexyl esters.

The alkali-metal alkoxides are the sodium, potassium and lithium methoxides, ethoxides, propoxide and butoxides. The alkoxides are used in the method of this invention in amounts sufficient to convert the hydroxyl groups on the benzoate to an alkali-metal oxy group. Preferably, the alkoxides are present in amounts ranging from about 0.95 mol % to about 1.05 mol % based on the benzoate.

The alkylene glycols useful for this invention are those having from 2 to 10 carbon atoms. Preferably, the glycols have the formula $HO(CH_2)_nOH$ wherein n is an integer of from 2 to 10. Other glycols include the gem dialkyl glycols, e.g., neopentyl glycol. Diethylene glycol is also used as the glycol solvent-reactant of this invention. The glycols are employed in amounts sufficient to interchange with the alkyl ester group of the benzoate and also to maintain the reaction product in solution. Preferably, the glycol is present in a weight ratio ranging from about 0.67 to about 9.0 based on the benzoate.

The alkane sultones used for this invention are propane sultone and butane sultone. These compounds are used in amounts sufficient to theoretically convert all of the alkali-metal oxy groups to alkoxysulfonate salt groups. Preferably, the alkane sultones are used in amounts ranging from 0.95 mol % to about 1.05 mol based on the benzoate.

The temperatures and times used for the preparation of salts of alkoxysulfonated benzoic acid are well known to those skilled in this art, and from the standpoint of commercial use, temperatures ranging from about 60 to 80° C. are preferred with reaction times ranging from about one to three hours.

The salts produced in accordance with this invention are preferably used in amounts ranging from about 0.5 to about 5 mol % in filament-forming polyester resins to enhance their cationic dyeability. The preferred polyester resin is one formed from terephthalic acid and ethylene glycol although as well known in this art other dicarboxylic acids alone or in mixtures and diols alone or in mixtures can be used for the resin preparation.

The following example is set forth to demonstrate this invention.

EXAMPLE 2530 mls. of ehtylene glycol, 1728 grams of a 25 weight percent solution of sodium methoxide in methanol and 1216 grams of methyl 3-hydroxybenzoate were charged to a 12 liter flask, stirred and heated to 65° C. To this reaction mixture, which contains the sodium salt of methyl 3-hydroxybenzoate and the sodium salt of 2-hydroxyethyl 3-hydroxybenzoate, was added 976 grams of propane sultone over a 20 minute period. The tempeature rose to 80° C. during the addition of the propane sultone. When addition was complete, the reaction mixture was held for two hours at 75–80° C., heat being applied as necessary to maintain this temperature. At the end of two hours the methanol was distilled off. The mixture was assayed and 1430 mls. of ethylene glycol was added to dilute the solution to 40 weight percent of the product, 2-hydroxyethyl 3-(3-sodiumsulfopropoxy) benzoate.

This solution was added to a reactor along with dimethyl terephthalate, ethylene glycol and catalysts. The mixture was subjected to conventional transesterification and polycondensation procedures to produce a filament-forming resin containing on the polymer chain about 2 mol percent of the sodium salt of m-propoxy sulfonated benzoic acid methyl ester. The resin was melt spun and processed into textile yarn. This yarn showed much improved cationic dyeability over yarn produced from ethylene terephthalate homopolymer resin.

Various changes and modifications may be made in practicing the invention without departing from the spirit and scope thereof and, therefore, the invention is not to be limited except as defined in the appended claims.

We claim:

1. A method of preparing an alkali-metal salt of an alkoxysulfonated benzoic acid glycol ester which comprises reacting an alkyl ester of a meta- or para-hydroxy substituted benzoic acid wherein the alkyl group has from 1 to 6 carbon atoms with an alkali-metal alkoxide wherein the alkoxide group has from 1 to 4 carbon atoms and a solvent-reactant consisting essentially of an alkylene glycol having from 2 to 10 carbon atoms or diethylene glycol whereby a glycol ester of an alkali-metal oxy substituted benzoic acid is formed, and reacting said glycol ester with an alkane sultone having from 3 to 4 carbon atoms to form an alkali-metal salt of an alkoxy sulfonated benzoic acid glycol ester dissolved in said solvent-reactant glycol.

2. The method of claim 1 wherein the alkali-metal alkoxide is sodium methoxide and the sodium methoxide is dissolved in methanol.

3. The method of claim 1 wherein the alkylene glycol is ethylene glycol.

4. The method of claim 1 wherein the alkane sultone is propane sultone.

5. The method of claim 1 wherein the alkyl ester of meta- or para-hydroxy substituted benzoic acid is the methyl ester of meta-hydroxy substituted benzoic acid.

6. The method of claim 1 wherein the alkyl ester of meta- or para-hydroxy substituted benzoic acid is the methyl ester of para-hydroxy substituted benzoic acid.

7. The method of claim 1 wherein the formed alkali-metal salt of an alkoxysulfonated benzoic acid glycol ester dissolved in said solvent-reactant glycol is combined with dimethyl terephthalate and ethylene glycol, and the mixture subjected to transesterification and polycondensation reaction conditions to form a filament-forming copolyester resin containing about 0.5 to about 5 mol % of said alkali-metal salt.

8. The method of claim 1 wherein the formed alkali-metal salt of an alkoxysulfonated benzoic acid glycol ester dissolved in said solvent-reactant glycol is combined with the prepolymer product of the direct esterification of terephthalic acid and ethylene glycol, and the mixture subjected to polycondensation conditions to form a filament-forming copolyester resin containing about 0.5 to about 5 mol % of said alkali-metal salt.

* * * * *